(12) United States Patent
Kim et al.

(10) Patent No.: US 8,752,415 B2
(45) Date of Patent: Jun. 17, 2014

(54) METHOD AND SYSTEM FOR MEASURING ENGINE OIL DETERIORATION

(75) Inventors: Won Gyu Kim, Seoul (KR); Ki Hwan Oh, Seoul (KR); Keun Woo Chung, Gongju-si (KR); Young-Wun Kim, Daejeon (KR)

(73) Assignees: Hyundai Motor Company, Seoul (KR); Korea Research Institute of Chemical Technology, Daejeon (KR)

( * ) Notice: Subject to any disclaimer, the term of this patent is extended or adjusted under 35 U.S.C. 154(b) by 246 days.

(21) Appl. No.: 13/316,531

(22) Filed: Dec. 11, 2011

(65) Prior Publication Data

US 2013/0047708 A1 Feb. 28, 2013

(30) Foreign Application Priority Data

Aug. 30, 2011 (KR) ........................ 10-2011-0087247

(51) Int. Cl.
*G01N 21/59* (2006.01)

(52) U.S. Cl.
USPC ... 73/53.07; 73/53.05; 73/61.48; 250/339.07; 250/339.11; 250/341.8

(58) Field of Classification Search
USPC ................ 73/53.05, 53.07, 61.48; 250/336.1, 250/338.1, 339.06, 339.07, 339.11, 341.8, 250/343
See application file for complete search history.

(56) References Cited

U.S. PATENT DOCUMENTS

| | | | | |
|---|---|---|---|---|
| 3,526,127 | A * | 9/1970 | Sarkis | 73/53.05 |
| 4,570,069 | A * | 2/1986 | Gager | 250/343 |
| 4,677,847 | A * | 7/1987 | Sawatari et al. | 73/53.05 |
| 5,049,742 | A * | 9/1991 | Hosonuma et al. | 250/301 |
| 5,382,942 | A * | 1/1995 | Raffa et al. | 340/457.4 |
| 5,420,041 | A * | 5/1995 | Matsushita et al. | 436/61 |
| 5,548,393 | A * | 8/1996 | Nozawa et al. | 356/70 |
| 5,569,842 | A * | 10/1996 | Silvestri | 73/53.05 |
| 5,604,441 | A * | 2/1997 | Freese et al. | 324/663 |
| 6,061,139 | A * | 5/2000 | Takezawa et al. | 356/407 |
| 6,253,601 | B1 * | 7/2001 | Wang et al. | 73/114.55 |
| 6,690,452 | B2 * | 2/2004 | Wilks, Jr. | 356/70 |
| 6,741,938 | B2 * | 5/2004 | Berndorfer | 702/23 |
| 7,136,155 | B2 * | 11/2006 | Kong et al. | 356/70 |
| 7,160,728 | B2 * | 1/2007 | Chimenti et al. | 436/29 |
| 7,172,903 | B2 * | 2/2007 | Schilowitz et al. | 436/60 |
| 7,339,657 | B2 * | 3/2008 | Coates | 356/73 |
| 7,716,972 | B2 * | 5/2010 | Preston | 73/114.55 |
| 7,907,282 | B2 * | 3/2011 | Coates | 356/419 |

(Continued)

FOREIGN PATENT DOCUMENTS

| | | | | |
|---|---|---|---|---|
| JP | 63009863 A * | 1/1988 | | G01N 33/28 |
| JP | 07146233 A * | 6/1995 | | G01N 21/59 |
| JP | 09229847 A * | 9/1997 | | |
| JP | 3034914 B2 | 2/2000 | | |

(Continued)

*Primary Examiner* — David A Rogers
(74) *Attorney, Agent, or Firm* — Morgan, Lewis & Bockius LLP

(57) ABSTRACT

The present invention relates to a method of measuring engine oil deterioration, including measuring the first absorbance of engine oil using near infrared at a wavelength of 1000 nm or more, measuring the second absorbance of the engine oil during use using near infrared at the wavelength, and comparing the first absorbance and the second absorbance of the engine oil, so that the engine oil may be determined to be in a state of deterioration when the second absorbance may be at least 1.5 times the first absorbance, and to a system for measuring engine oil deterioration therefor.

3 Claims, 2 Drawing Sheets

(56) References Cited

U.S. PATENT DOCUMENTS

| | | | |
|---|---|---|---|
| 8,222,605 B2* | 7/2012 | Da Silva et al. | 250/339.08 |
| 2003/0060984 A1* | 3/2003 | Takezawa et al. | 702/28 |
| 2003/0164451 A1* | 9/2003 | Reischman et al. | 250/339.12 |
| 2008/0024761 A1* | 1/2008 | Kong et al. | 356/70 |
| 2010/0157304 A1* | 6/2010 | Takahashi et al. | 356/442 |
| 2010/0180671 A1* | 7/2010 | Okuyama et al. | 73/53.05 |

FOREIGN PATENT DOCUMENTS

| | | | |
|---|---|---|---|
| JP | 2000146696 A | * | 5/2000 |
| JP | 2005-521862 A | | 7/2005 |
| JP | 2007198767 A | * | 8/2007 |
| KR | 1999-0040786 A | | 6/1999 |
| KR | 10-0302643 B1 | | 7/2001 |
| KR | 10-2009-0005850 A | | 1/2009 |

* cited by examiner

METHOD AND SYSTEM FOR MEASURING ENGINE OIL DETERIORATION

CROSS-REFERENCE TO RELATED APPLICATION

The present application claims priority to Korean Patent Application No. 10-2011-0087247, filed on Aug. 30, 2011, the entire contents of which is incorporated herein for all purposes by this reference.

BACKGROUND OF THE INVENTION

1. Field of the Invention

The present invention relates to a method and system for measuring engine oil deterioration, which is very reliable because it enables the objectification of measurement while easily measuring the deterioration of engine oil.

2. Description of Related Art

The engine oil of vehicles deteriorates when used for a long period of time, and the oil gradually changes from alkaline to acidic depending on the use thereof. Thus, a total base number (TBN) of oil gradually decreases depending on the use of the oil. The degree of deterioration of oil may be accurately detected by TBN.

However, because a device for measuring the TBN is difficult to mount in vehicles, a variety of alternatives thereto have been devised.

For example, based on the fact that the viscosity increases when the oil deteriorates, methods have been proposed that measure changes in the viscosity of oil using a pressure sensor that measures the pressure difference of an oil passage or the discharge pressure of an oil pump. However, the deterioration of oil cannot necessarily be considered to be the only cause of such a pressure difference, and the measurement deviation thereof is very large, and such methods are not generalized.

On the other hand, a technique wherein an electrode for measuring capacitance is mounted in order to measure changes in polar groups due to the deterioration of oil is disclosed in Korean Patent Publication No. 10-2001-0009114. In this case, there are various factors that have an influence on the capacitance, and such changes are very small, and the limitation of measurement errors is imposed on the measured values, making it unsuitable to actually mount such an electrode to vehicles.

Therefore, there are urgently required measurement standards, methods and systems, which enable easy and simple measurement and ensure reliable determination with high accuracy.

This related art is merely utilized to enhance understanding about the background of the present invention, and should not be regarded as conventional techniques known to those having ordinary knowledge in the art.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a method and system for measuring engine oil deterioration, which enables taking measurements to be comparatively easy and simple and may ensure reliable determination with high accuracy.

In an aspect of the present invention, a method of measuring engine oil deterioration, may include measuring a first absorbance of engine oil using near infrared at a wavelength of 1000 nm or more, measuring a second absorbance of the engine oil during use using near infrared at the wavelength, and comparing the first absorbance and the second absorbance of the engine oil, so that the engine oil is determined to be in a state of the engine oil deterioration when the second absorbance is at least 1.5 times the first absorbance.

The near infrared may have a wavelength of 1100~1300 nm.

The measuring the first absorbance is performed by measuring an initial absorbance upon injection of the engine oil into a vehicle.

In another aspect of the present invention, a method of measuring engine oil deterioration, may include measuring a first absorbance of engine oil using near infrared at a wavelength of 1000 nm or more, measuring a second absorbance of the engine oil during use using near infrared at the wavelength, multiplying a difference between the first absorbance and the second absorbance of the engine oil by a square of a daily average mileage, thus determining a determination value, and determining the engine oil to be in a state of the engine oil deterioration when the determination value is 500 or more.

The engine oil is determined to be in the state of the engine oil deterioration when the second absorbance of the engine oil during use is at least 1.5 times the first absorbance.

In further another aspect of the present invention, a system for measuring engine oil deterioration may include an absorbance measurement part for measuring a first absorbance of engine oil using near infrared at a wavelength of 1000 nm or more, and a deterioration determination part for determining a ratio of increase of a second absorbance relative to the first absorbance of the engine oil, so that the engine oil is determined to be in a state of the engine oil deterioration when the ratio of increase is at least 1.5.

In the absorbance measurement part the near infrared may have a wavelength of 1100~1300 nm.

The first absorbance is an initial absorbance upon injection of the engine oil into a vehicle.

In a still further aspect of the present invention, a system for measuring engine oil deterioration, may include an absorbance measurement part for measuring a first absorbance of engine oil using near infrared at a wavelength of 1000 nm or more, a mileage determination part for determining a daily average mileage, and a deterioration determination part for determining a determination value by multiplying a difference between the first absorbance and a second absorbance of the engine oil by a square of the daily average mileage, so that the engine oil is determined to be in a state of the engine oil deterioration when the determination value is 500 or more.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
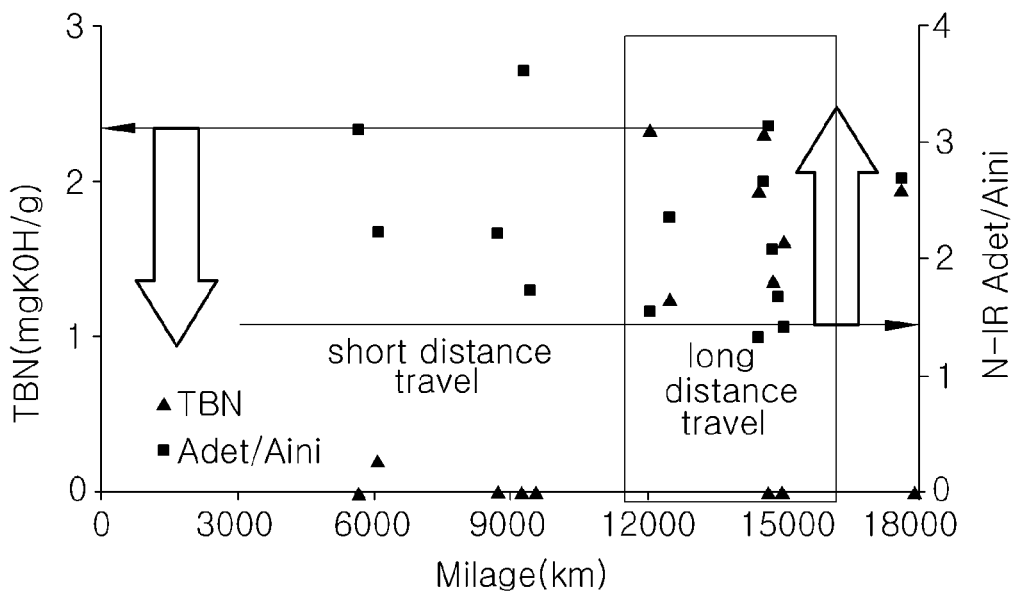
FIG. 1 is a graph showing TBN with respect to a long distance travel and a short distance travel.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, a method and system for measuring engine oil deterioration according to preferred embodiments of the present invention will be described with reference to the accompanying drawings.

According to an exemplary embodiment of the present invention, a method of measuring engine oil deterioration includes measuring the first absorbance of engine oil using near infrared (N-IR) at a wavelength of 1000 nm or more, measuring the second absorbance of the engine oil during use using N-IR at the above wavelength, and comparing the first absorbance and the second absorbance of the engine oil during use, so that the engine oil is determined to be in a state of deterioration when the second absorbance is at least 1.5 times the first absorbance.

In an exemplary embodiment of the present invention, the degree of deterioration of the engine oil is measured using N-IR at a wavelength of 1000 nm or more. The degree of deterioration of the engine oil detectable from the N-IR absorbance should be able to be uniformly applied for any travel frequency, including cases where the mileage is short or long.

Also, in the case where the first absorbance is regarded as an initial absorbance upon injection of engine oil into a vehicle, results much closer to actual values may be attained, and the following is a description of an exemplary embodiment based on the assumption that the first absorbance is the initial absorbance.

FIG. 1 is a graph showing the TBN with respect to a long distance travel and a short distance travel, namely, the relationship of TBN and N-IR Adet/Aini (N-IR absorbance during travel/initial absorbance) of short-travel vehicles used to commute and long-travel vehicles that have a daily average mileage of 50 km or longer. In the above graph showing the test results, the case where all of short- and long-travel vehicles have a TBN of 2.3 or less (which is the actual point of time of deterioration regarded as the exchange time of oil) corresponds to the case where an N-IR increase is at least 1.5. As such, the N-IR increase indicates the value of N-IR Adet/Aini (N-IR absorbance during travel/initial absorbance).

Hence, upon long distance driving, the exchange cycle of engine oil was determined in the mileage range of 12000~15000 km corresponding to the case where the N-IR increase is at least 1.5, and in short-travel vehicles, the exchange cycle of engine oil was determined in the mileage range of 600~9000 km corresponding to the case where the N-IR increase is at least 1.5. These results were in accord with actual exchange cycles.

Thus in the method of measuring engine oil deterioration according to an exemplary embodiment of the present invention, measuring the initial absorbance of engine oil using N-IR at a wavelength of 1000 nm or more and measuring the absorbance of engine oil during use using N-IR at the above wavelength in real time are carried out.

Further, the initial absorbance and the absorbance of engine oil during use are compared, so that engine oil is determined to be in a state of deterioration when the absorbance of engine oil during use is at least 1.5 times the initial absorbance. Thereby, the TBN value from which the actual deterioration time of engine oil may be determined may be indirectly checked, and thus measurement is objectified ultimately increasing measurement reliability.

On the other hand, the N-IR used has a wavelength of 1100~1300 nm. A variety of test results showed that the wavelength of N-IR close to the results of FIG. 1 is 1100~1300 nm. In particular, considerably accurate results were obtained at 1211 nm. This conclusion resulted from measuring the wavelength range in which an increase in absorbance was well observed when the absorbance of engine oil was measured using N-IR at a variety of wavelengths.

Also, measuring the absorbance of the engine oil during use may further include multiplying a difference between the initial absorbance and the absorbance of the engine oil during use by a square of a daily average mileage thus calculating a determination value, and comparing the initial absorbance and the absorbance of the engine oil during use may be used to allow it to be determined that the engine oil is in a state of deterioration when the absorbance of the engine oil during use is at least 1.5 times the initial absorbance and the determination value is 500 or more.

Figure 2:
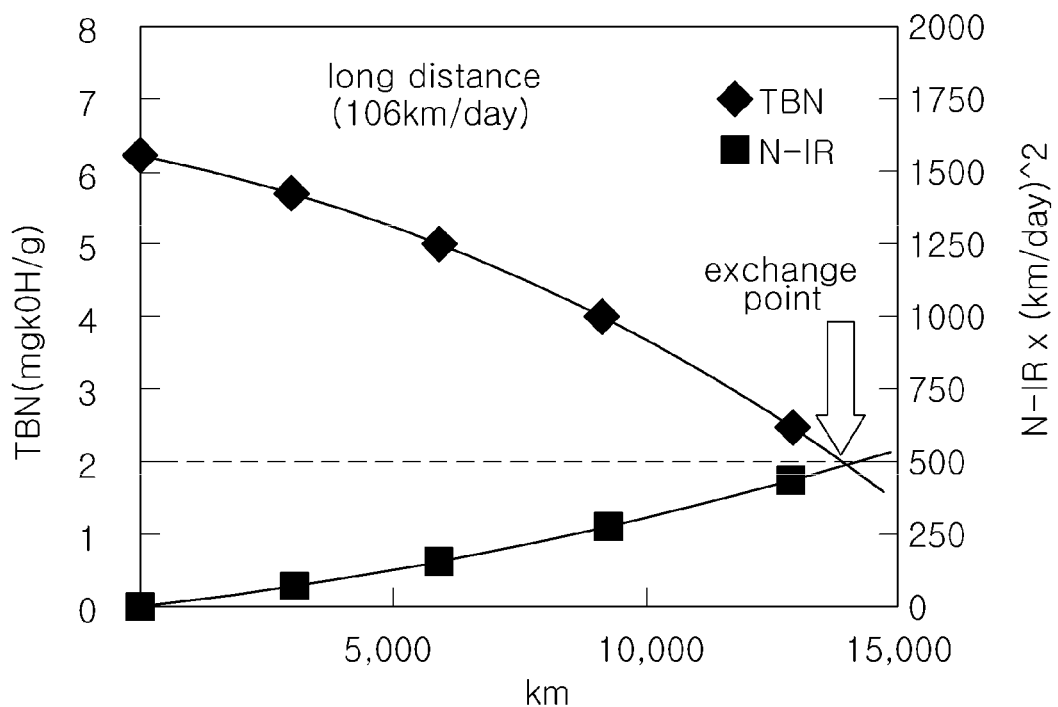
FIG. 2 is a graph showing the results when applying a process of measuring engine oil deterioration according to an exemplary embodiment of the present invention to a long distance travel.
Figure 3:
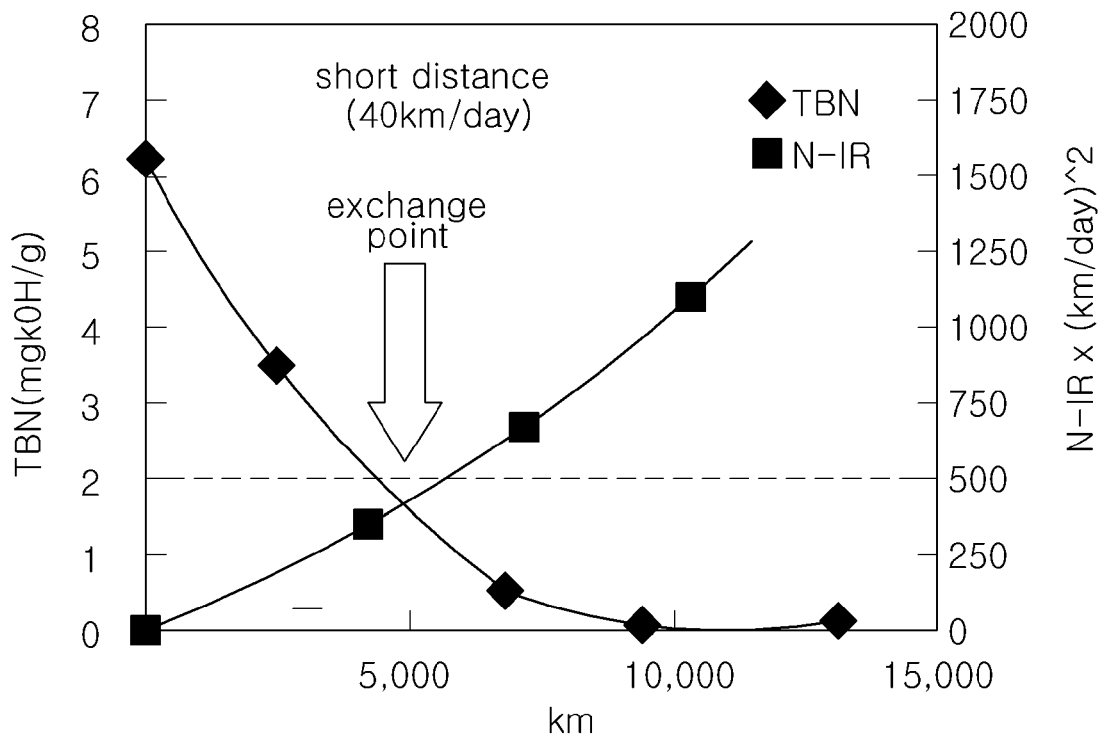
FIG. 3 is a graph showing the results when applying the process of measuring engine oil deterioration according to the exemplary embodiment of the present invention to a short distance travel.

FIG. 2 is a graph showing the results when applying the process of measuring engine oil deterioration according to an exemplary embodiment of the present invention to a long distance travel, and FIG. 3 is a graph showing the results when applying the process of measuring engine oil deterioration according to the exemplary embodiment of the present invention to a short distance travel.

As shown in the graph of FIG. 2 corresponding to long distance driving at a daily average mileage of 106 km, when the determination value (N–IR*[km/day]^2) obtained by multiplying the difference between the initial absorbance and the absorbance of the engine oil during use by the square of the daily average mileage exceeds 500, the actual TBN may be 2.0 or below. Thus, in the case of a long distance travel, the point of time at which engine oil is determined to be deteriorated corresponds to the case where the determination value is 500 or more.

In FIG. 3 showing short distance driving, the point of time at which engine oil is determined to be deteriorated corresponds to the case where the determination value is 500 or more. In this case, the TBN is decreased to 2.0 or less.

According to these test results, in both long distance driving and short distance driving, the actual deterioration time of engine oil may be efficiently predicted by the determination value resulting from multiplying the difference between the initial absorbance and the absorbance of the engine oil during use by the square of the daily average mileage.

To generate test results, the method of measuring engine oil deterioration according to an exemplary embodiment of the present invention may include measuring the initial absorbance of engine oil using N-IR at a wavelength of 1000 nm or more, measuring the absorbance of the engine oil during use using N-IR at the above wavelength, multiplying the difference between the initial absorbance and the absorbance of the engine oil during use by the square of the daily average mileage, thus calculating the determination value, and determining the engine oil to be in a state of deterioration when the determination value is 500 or more.

Figure 4:
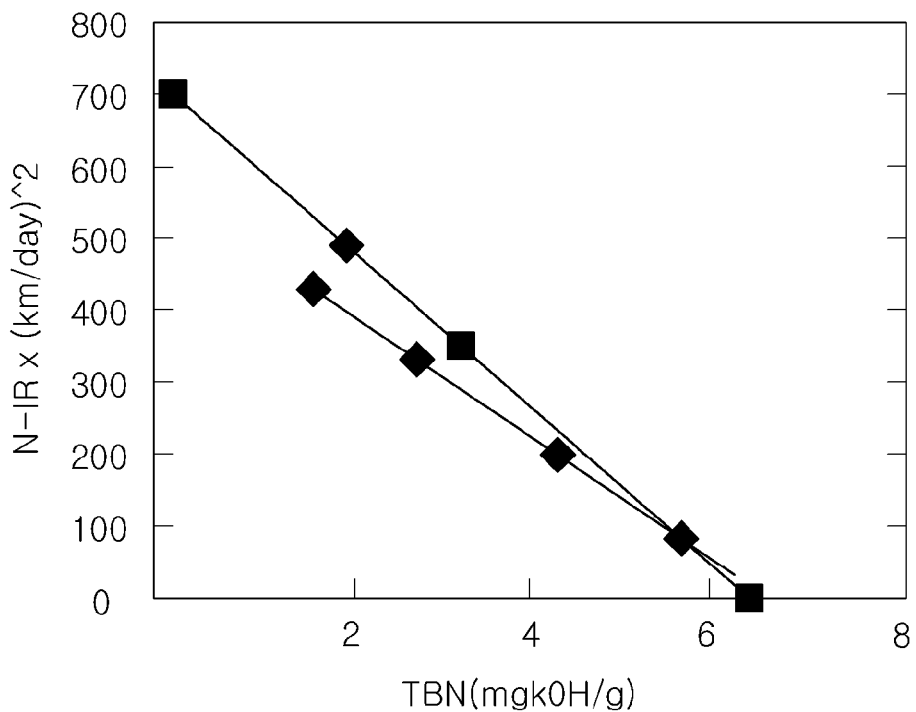
FIG. 4 is a graph showing the relationship between mileage and TBN.

FIG. 4 is a graph showing the relationship between mileage and TBN. In both long distance driving and short distance driving, the moment at which TBN is decreased to 2.0 or less corresponds to the case where the determination value is 400 or 500 or more. Particularly the case where the determination value is 500 or more is regarded as very reasonable in terms of exchanging the engine oil.

In addition, the system for measuring engine oil deterioration, which embodies the method of measuring engine oil deterioration according to an exemplary embodiment of the present invention, includes an absorbance measurement part for measuring the absorbance of engine oil using N-IR at a wavelength of 1000 nm or more, and a deterioration determination part for calculating a ratio of increase of the absorbance of engine oil during use relative to the initial absorbance of engine oil, so that the engine oil is determined to be in a state of deterioration when the ratio of increase is at least 1.5.

In the absorbance measurement part, the N-IR may have a wavelength of 1100 1300 nm.

The system for measuring engine oil deterioration may further include a mileage calculation part for calculating a daily average mileage, and the deterioration determination part may determine the engine oil to be in a state of deterioration when the ratio of increase of the absorbance of the engine oil during use relative to the initial absorbance is at least 1.5 and when the determination value obtained by multiplying the difference between the initial absorbance and the absorbance of the engine oil during use by the square of the daily average mileage is 500 or more.

The system for measuring engine oil deterioration according to an exemplary embodiment of the present invention is a real-time engine oil deterioration measurement system, and may thus be configured to include a display device for showing the exchange time of engine oil on a dashboard of a vehicle, an IR sensor for measuring the degree of deterioration of engine oil, and a system for converting the degree of deterioration to an electrical signal.

The degree of deterioration of the engine oil is represented by a signal on the dashboard in both cases of the N-IR absorbance being increased by at least 1.5 times the present absorbance value based on drastic changes in absorbance at a specific wavelength of 1211 nm and of the determination value obtained by multiplying the square of the average mileage by the absorbance correction being 500 or more, whereby the engine oil may be exchanged by a driver.

The sensor for measuring engine oil deterioration is mounted to the oil passage between an oil fan and a cylinder and the mounting position thereof may vary depending on the kind of vehicle.

As described hereinbefore, the present invention provides a method and system for measuring engine oil deterioration. According to an exemplary embodiment of the present invention, the system can be constructed to be small, and can be easily applied to vehicles because the deterioration of engine oil is determined using a comparatively inexpensive N-IR measurement device.

Also, according to an exemplary embodiment of the present invention, in the case where the deterioration of engine oil is determined based on the N-IR absorbance of the engine oil and the daily average mileage, an exchange cycle which considerably matches with an actual exchange cycle based on the TBN can be obtained, thus objectifying the measurement and the determination and attaining very reliable data.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of measuring engine oil deterioration, comprising:
    measuring a first absorbance of engine oil using near infrared at a wavelength of 1000 nm or more;
    measuring a second absorbance of the engine oil during use using near infrared at the wavelength;
    multiplying a difference between the first absorbance and the second absorbance of the engine oil by a square of a daily average mileage, thus determining a determination value; and
    determining the engine oil to be in a state of the engine oil deterioration when the determination value is 500 or more.

2. The method of claim 1, wherein the engine oil is determined to be in the state of the engine oil deterioration when the second absorbance of the engine oil during use is at least 1.5 times the first absorbance.

3. A system for measuring engine oil deterioration, comprising:
    an absorbance measurement part for measuring a first absorbance of engine oil using near infrared at a wavelength of 1000 nm or more;
    a mileage determination part for determining a daily average mileage; and
    a deterioration determination part for determining a determination value by multiplying a difference between the first absorbance and a second absorbance of the engine oil by a square of the daily average mileage, so that the engine oil is determined to be in a state of the engine oil deterioration when the determination value is 500 or more.

* * * * *